United States Patent
Oliva Solà et al.

(10) Patent No.: US 11,196,074 B2
(45) Date of Patent: Dec. 7, 2021

(54) REVERSIBLE BIO SENSITIZED PHOTOELECTRIC CONVERSION AND $H_2$ TO ELECTRICITY DEVICES

(71) Applicants: PROTON NEW ENERGY FUTURE, S.L, Mataró (ES); Cristina Oliva Solà, Terrassa (ES); Miquel Jove Peralta, Mataró (ES)

(72) Inventors: Cristina Oliva Solà, Terrassa (ES); Miquel Jove Peralta, Mataró (ES)

( * ) Notice: Subject to any disclaimer, the term of this patent is extended or adjusted under 35 U.S.C. 154(b) by 37 days.

(21) Appl. No.: 16/631,148

(22) PCT Filed: Jul. 13, 2018

(86) PCT No.: PCT/EP2018/069094
§ 371 (c)(1),
(2) Date: Jan. 14, 2020

(87) PCT Pub. No.: WO2019/012111
PCT Pub. Date: Jan. 17, 2019

(65) Prior Publication Data
US 2020/0227768 A1      Jul. 16, 2020

(30) Foreign Application Priority Data
Jul. 14, 2017   (EP) .................................... 17382464

(51) Int. Cl.
*H01M 8/18*    (2006.01)
*H01L 51/00*   (2006.01)
(Continued)

(52) U.S. Cl.
CPC ........ *H01M 8/186* (2013.01); *H01L 51/0093* (2013.01); *H01L 51/441* (2013.01); *H01M 14/005* (2013.01)

(58) Field of Classification Search
None
See application file for complete search history.

(56) References Cited

U.S. PATENT DOCUMENTS 4,215,182 A * 7/1980 Ang .................. H01M 8/18
                                                              429/500
2008/0131762 A1   6/2008 Joo et al.
(Continued)

FOREIGN PATENT DOCUMENTS

| DE | 10 2015 119159 A1 | 5/2016 |
| GB | 2501119 A | 10/2013 |
| WO | WO 2013/041086 A1 | 3/2013 |

OTHER PUBLICATIONS

International Search Report and Written Opinion dated Nov. 14, 2018 for Application No. PCT/EP2018/069094, 16 pages.
(Continued)

*Primary Examiner* — Eli S Mekhlin
(74) *Attorney, Agent, or Firm* — Squire Patton Boggs (US) LLP (57) ABSTRACT

The invention provides reversible bio sensitized photoelectric conversion and $H_2$ to electricity conversion devices which use one or more of a proton pumping photoactive biological layers to generate a proton gradient that is harnessed to produce electrical energy. It is also provided a photoelectric conversion element that incorporates the device of the present invention.

15 Claims, 3 Drawing Sheets

(51) Int. Cl.
*H01L 51/44* (2006.01)
*H01M 14/00* (2006.01)

(56) References Cited

U.S. PATENT DOCUMENTS

| | | |
|---|---|---|
| 2009/0229669 A1 | 9/2009 | Birge et al. |
| 2010/0200049 A1 | 8/2010 | Kufryk et al. |
| 2017/0200561 A1 | 7/2017 | Swiegers et al. |

OTHER PUBLICATIONS

Brillet, et al. "Examining architectures of photoanode-photovoltaic tandem cells for solar water splitting", *Journal of Materials Research* 2010, Jan. 2010, vol. 25, Issue 1, pp. 17-24.

Brimblecombe, et al. "A tandem water-splitting device based on a bio-inspired manganese catalyst", *ChemSusChem* 2010, Oct. 8, 2010, vol. 3, Issue 10, pp. 1146-1150.

Francas, et al. "A Ru-Hbpp-based water-oxidation catalyst anchored on Rutile TiO2", *ChemSusChem* 2009, Apr. 9, 2009, vol. 2, Issue 4, pp. 321-329.

Mahyad, et al. "Bio-nano hybrid materials based on bacteriorhodopsin: Potential applications and future strategies", *Advances in Colloid and Interface Science,* Sep. 26, 2015, vol. 225, No. 26, pp. 194-202.

Tran, et al. "Water electrolysis and photoelectrolysis on electrodes engineered using biological and bio-inspired molecular systems", *Energy and Environmental Science* 2010, Jun. 2010, vol. 3, No. 6, pp. 727-747.

\* cited by examiner

REVERSIBLE BIO SENSITIZED PHOTOELECTRIC CONVERSION AND $H_2$ TO ELECTRICITY DEVICES

This application is a 35 U.S.C. 371 filing of International Application No. PCT/EP2018/069094, filed on Jul. 13, 2018, which claims priority to and the benefit of European Patent Application No. EP 17382464.0, filed on Jul. 14, 2017, all of which are incorporated verbatim herein by reference in their entirety, including the specifications, drawings, and the claims.

The present disclosure relates to methods and devices for use in photoelectric conversion.

BACKGROUND ART

An important milestone in the solar cells was the invention of excitonic solar cell called dye sensitized solar cells (DSSC). In DSSC, light active synthetic dye (organic or organometallic) is usually bound to nanostructured wide gap metal oxide semiconductor and used as photo sensitized to harvest the solar energy and generate excitons. Bio-sensitized solar cells (BSSC) are based on the phenomenon of photon triggered electron ejection by light activated proteins. DSSC and BSSC systems differ mainly in the electron donor-synthetic dye in the former and light-activated biomolecules in the later.

Bacteriorhodopsin (bR), a membrane protein found in the archae *Halobacterium salinarum* is a natural light activated protein, holds high promise for solar energy conversion. bR has remarkable functional stability against a high concentration of salt (up to 5 M NaCl) and thermal stability even up to ~140° C., in dry state and with high quantum efficiency. In addition, bR functionally tolerates broad range of pH (5-11). It is easy and inexpensive to clone and express.

For engineered applications, bacteriorhodopsin is purified as membrane patches, known as purple membrane (PM). Purple membrane is a large cell membrane patch, which is composed of multiple bacteriorhodopsin molecules and their associated lipids. This structure provides it a high degree of chemical stability and resistance to thermal degradation. It is called PM due to its distinct purple color, which is due to its absorption peak near 570 nm. Purple membrane has been shown to maintain functionality at temperatures up to 80° C. in water and 140° C. dried. In the dried state, as well as the wet state, PM retains its light absorption properties and photochemical activity for years.

The use of bacteriorhodopsin for light scavenger devices dates back to earliest 90s. Since then, it has been studied the behavior of the protein and the biological cycle it performs for the proton pump when receiving sunlight and the direct application of the protein on conductive oxides to take advantage of the differential of potential that generates.

In J Nanoscience and Nanotech, 2009, 9, 1679-1687, Thavasi V. et al, it was described the operation of a solar plate based on $TiO_2$ nanoparticles with bR immobilized as a electrode ($FTO/TiO_2/bR$) and FTO/Al electrode in KCl electrolyte at pH 8. A short-circuit current of 0.089 $mA/cm^2$ and an open-circuit potential of 0.35 V was achieved under an excitation of 40 $mW/cm^2$. The study demonstrates the viability of the bacteria to be used as a charge generator through solar radiation. However, its approach does not contemplate taking advantage of the associated hydrogen generation.

The most promising field of use of bacteriorhodopsin as a base in a solar device is in harnessing its ability to separate and pump protons from water. However, adaptations must be made, such as the addition of a polymer layer (Nafion) that only passes the protons, creating a potential differential between the medium (water) and the other end of the polymer layer. This type of technology is the one that is currently used in fuel cells.

In U.S. Pat. No. 9,023,989 it is described a photovoltaic cell based on bacteriorhodopsin, exposing how the protein can be targeted on a substrate and modified by mutations to improve transmembrane proton transfer and covalent attachment between the protein and the substrate. However, despite describing that these photovoltaic cells based on bacteriorodpsin generate hydrogen gas from water and can be harnessed to produce electricity, it does not expose any design how to take advantage of this hydrogen.

In Adv. Colloid and Interface Sci. 2015, 225: 194-202 it is disclosed bio-nano hybrid materials based on bacteriorhodopsin conjugated to different nanomaterials and its application in solar $H_2$ generation systems.

SUMMARY

Figure 1:
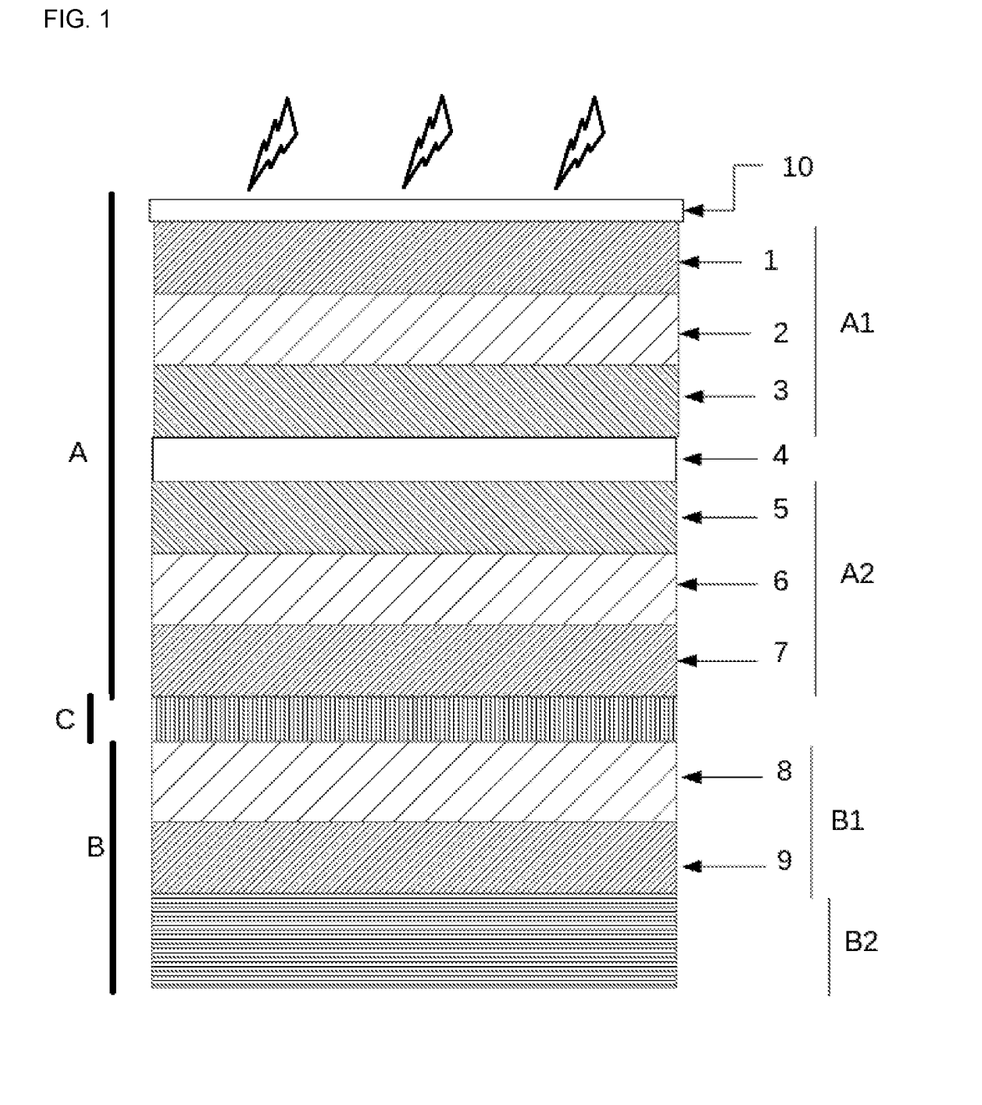
FIG. 1 represent a cross-sectional view of the bio sensitized photoelectric conversion device according to an embodiment of the present invention.

The present invention provides a reversible bio sensitized photoelectric conversion and $H_2$ to electricity conversion device comprising a first compartment (A) and a second compartment (B); the first compartment (A) comprises a first photoanode electrode (A1) and a second electrode (A2) with a water-containing medium (4) therebetween; wherein a polymeric membrane (C) is disposed between the first compartment (A) and the second compartment (B); the second compartment (B) comprises a third electrode (B1), and an hydrogen collecting deposit (B2).

The reversible bio sensitized photoelectric conversion and $H_2$ to electricity conversion device of the invention comprises the following elements extending from its front end surface to its opposing back end surface, which corresponds with the direction of incident light (c.f. FIG. 1):

i) a first compartment (A) which comprises a first photoanode electrode (A1), and a second electrode (A2), which may work as an anode or as a cathode, with a water-containing medium (4) therebetween;
ii) a polymeric membrane (C) disposed between the first compartment (A) and the second compartment (B); and
iii) a second compartment (B) which comprises a third electrode (B1), which may work as a cathode or as an anode depending of the role of the second electrode (A2) being opposite to it, and an hydrogen collecting deposit (B2);
wherein
the first compartment (A), extending from its front end surface to its opposing back end surface (i.e. in the direction of incident light), comprises:
  i.1 a first photoanode electrode (A1) which comprises:
    i.1.1 a layer of a visible or UV and visible radiation transparent conductor material (1);
    i.1.2 a first conductive metallic material (2); and
    i.1.3 optionally, one or more of a proton pumping photoactive biological layers (3) comprising oriented purple membrane containing bacteriorhodopsin protein or any of its genetic variants; stabilized bacteriorhodopsin protein-based sensitizer or any of its genetic variants; or mixtures thereof;
  the proton pumping photoactive biological layers (3) being deposited on the first conductive metallic material (2);
  i.2 a water-containing medium (4);
  i.3. a second electrode (A2) which comprises:
    i.3.1 optionally, one or more of a proton pumping photoactive biological layers (5) comprising oriented purple membrane containing bacteriorhodopsin protein or any of its genetic variants; stabilized bacteriorhodopsin protein-based sensitizer or any of its genetic variants; or mixtures thereof; and i.3.2 a second conductive metallic material (6); the proton pumping photoactive biological layers (5) being deposited on the second conductive metallic material (6); and i.3.3 a layer of a visible or UV and visible radiation transparent conductor material (7);

with the proviso that at least one of the proton pumping photoactive biological layers (3) or (5) are present.

Accordingly, the present invention relates to a reversible bio sensitized photoelectric conversion and $H_2$ to electricity conversion device comprising one or more of a proton pumping photoactive biological layers comprising oriented purple membrane which contains bacteriorhodopsin protein or any of its genetic variants; stabilized bacteriorhodopsin protein-based sensitizer or any of its genetic variants; or mixtures thereof; the proton pumping photoactive biological layers being deposited on the surface of the first conductive metallic material of the first phothoanode electrode and on the second conductive metallic material of the second electrode.

The presence of the proton pumping photoactive biological layers, results in the generation of a proton gradient when sunlight (or any other suitable visible radiation) incides to it. Thus, it can be used to generate an electrical current and hydrogen gas via photoelectric-based water splitting; the hydrogen thus generated may be stored in the hydrogen collecting deposit (B2). When the system operates in the reverse mode, hydrogen is supplied from the hydrogen collecting deposit (B2) in order to generating electricity.

Accordingly, in the context of the present disclosure, the term "reversible bio sensitized photoelectric conversion and $H_2$ to electricity conversion device" means that it may operate in both modes: a direct mode for the generation of electric current and hydrogen by solar radiation via water splitting, and a reverse mode for the generation of an electric current with supply of hydrogen.

In general terms, overall water-splitting reaction comprises that the photocatalyst absorbs photon energy greater than the band-gap energy of the material and generates photo-excited electron hole pairs. Under irradiation, electrons in the valence band of the semiconductor photocatalyst are excited into the conduction band, leaving holes in the valence band. These photo-generated electrons and holes cause reduction of $H^+$ to $H_2$ and oxidation of $H_2O$ to $O_2$, respectively.

The following basic reaction scheme can be proposed for the water splitting reaction occurring in the direct mode of operation according to the present invention:

i) In compartment (A) (electrodes (A1) and (A2) are working as anodes)

$$4H_2O \rightarrow 4H^+ + 4OH^-$$

$$4OH^- \rightarrow 4e^- + 2H_2O + O_2$$

$$2H_2O \rightarrow 4H^+ + O_2$$

ii) In compartment (B) (electrode (B1) is working as cathode)

$$4H^+ + 4e^- \rightarrow 2H_2$$

Whereas, when the system operates in the reverse mode, the reaction scheme occurring is as follows:

i) In compartment (B) (electrode (B1) is working as anode)

$$H_2 \rightarrow 2H^+ + 2e^-$$

ii) In compartment (A) (electrode (A2) is working as cathode)

$$4e^- + 4H^+ + O_2 \rightarrow H_2O$$

Therefore, the reversible bio sensitized photoelectric conversion and $H_2$ to electricity conversion device of the invention is closed and reversible, which may be used in both processes:

i) water splitting for hydrogen generation with the correspondent energy production; and ii) generation of electric current by hydrogen conversion.

The innovation is a device closed, so it can be commercialized as solar module or solar glass, using personalized size to adapt the module, and generate the electricity in the same place where it is consumed, avoiding the transport. Other known devices with similar functionality as those disclosed in documents mentioned above are open systems, supplying input components to ensure a correct functionality. Furthermore, open systems are applied in huge electricity installations in order to produce hydrogen or electricity. The device works in the range of visible or visible and UV light, thus it can be used outdoor, both in sunny or in adverse weather conditions (i.e. shadows, storms or cloudy), and indoor.

The present device is reversible. Thus, the device produces electricity and hydrogen simultaneously in direct mode, storing the hydrogen inside the system. Additionally, in reverse mode, it is used when there is no visible light or direct light to convert de hydrogen stored in electricity. The reverted mode is acting as a battery, because hydrogen can be stored and later on converted it into electricity depending on the energy demand. The possibility to use the hydrogen deposit as a battery allows the device supplying energy at night, reducing space, and reducing costs because no battery is needed. The invention also provides a photoelectric conversion element that incorporates the bio sensitized photoelectric conversion device as defined herein. Preferably, the photoelectric conversion element is a solar cell.

BRIEF DESCRIPTION OF THE DRAWINGS

Non-limiting examples of the present disclosure will be described in the following, with reference to the appended drawings, in which.

DETAILED DESCRIPTION OF THE INVENTION

Throughout the figures the same reference numbers will be used for matching parts.

In some embodiments, the first photoanode electrode (A1) comprises one or more of a proton pumping photoactive biological layers (3).

In accordance with some embodiments, the second electrode (A2) comprises one or more of a proton pumping photoactive biological layers (5).

Alternatively, in accordance with some embodiments, both the first photoanode electrode (A1) and the second electrode (A2) comprise one or more of a proton pumping photoactive biological layers (3) and (5).

The reversible bio sensitized photoelectric conversion and $H_2$ to electricity conversion device of the present invention uses one or more of a proton pumping photoactive biological layers comprising oriented purple membrane which contains bacteriorhodopsin protein or any of its genetic variants; stabilized bacteriorhodopsin protein-based sensitizer or any of its genetic variants; or mixtures thereof; to generate a proton gradient that is harnessed to produce electrical energy and hydrogen.

It is known in the art that under oxygen limited conditions the *Halobacterium* cell grows planar purple membrane (PM) patches in the form of a hexagonal two-dimensional crystalline lattice of bR trimers. In accordance with an embodiment of the present invention, the proton pumping photoactive biological layer present in the first photoanode electrode, the second electrode, or both, may comprise oriented purple membrane which contains bacteriorhodopsin protein or any of its genetic variants.

Alternatively, in accordance with an embodiment of the present invention, the one or more proton pumping photoactive biological layers present in the first photoanode electrode, the second electrode, or both, may comprise stabilized bacteriorhodopsin protein-based sensitizer or any of its genetic variants.

Stabilized bacteriorhodopsin protein-based sensitizer refers to protein-based sensitizer derived from bacteriorhodopsin protein which has been stabilized. Stabilization can be accomplished by mixing the bacteriorhodopsin-based sensitizer with a surfactant. A preferred class of surfactants is protein stabilizing surfactants, such as peptide surfactants.

The terms "wild type bacteriorhodopsin" and "native bacteriorhodopsin", as used herein, both refer to the form of bacteriorhodopsin as it occurs in nature. Further, as used herein, the terms "mutant bacteriorhodopsin", "mutated bacteriorhodopsin" and "bacteriorhodopsin genetic variant" all refer to a bacteriorhodopsin protein in which the amino acid sequence of a wild type or native bacteriorhodopsin protein has had at least one of its amino acids replaced with a different amino acid.

There are different native *Halobacterium salinarum* strains accessible both in commercial sources and from different international depositary authorities under the Budapest Treaty. Thus, for example, *H. salinarum* S9 and L3 strains are commercially accessible.

Additionally, it is known that bacteriorhodopsin is formed by a proteic part, named bacterioopsin and a retinal unit. Bacterioopsin is codified by gen bop. Cloning and sequence analysis of a *H. halobium* DNA fragment that includes the structural gene for bacteriorhodopsin and sequences flanking the $NH_2$ and COOH termini was described in Proc. Natl Acad. Sci. USA 78/11 (1981) 6744-6748.

The skilled person in the art knows different methods of site-directed mutagenesis, such as Dunn, R., et al., The bacteriorhodopsin gene. Proc Natl Acad Sci USA, 1981. 78(11) 6744-6748; Landt, O., H. P. Grunert, and U. Hahn, A general method for rapid site-directed mutagenesis using the polymerase chain reaction. Gene, 1990. 96(1) 125-128; and Juncosa-Ginesta, M., et al., Improved efficiency in site-directed mutagenesis by PCR using a *Pyrococcus* sp. GB-D polymerase. Biotechniques, 1994. 16(5) 820-823.

As mentioned above, and shown in FIG. 1, the reversible bio sensitized photoelectric conversion and $H_2$ to electricity conversion device comprises a first compartment (A) and a second compartment (B); the first compartment (A) comprises a first photoanode electrode (A1) and a second electrode (A2) with a water-containing medium (4) therebetween; wherein a polymeric membrane (C) is disposed between the first compartment (A) and the second compartment (B); the second compartment (B) comprises a third electrode (B1), and an hydrogen collecting deposit (B2).

The first compartment (A) extends from a front end surface to an opposing back end surface (which corresponds with the direction of incident light, c.f. FIG. 1), wherein the front end surface of compartment (A), when the bio sensitized photoelectric conversion device of the invention is in use, it is irradiated with an incident light.

In some embodiments, the incident light may be natural sunlight or any type of radiation source having a wavelength in the central range of the solar spectrum. Generally, incident light comprising a wavelength in the 280-1100 nm region may be used. Preferably in the 350-850 nm region, being particularly preferred in the 500-650 nm region.

In accordance with some embodiments of the present invention, the layer of a UV and visible radiation transparent conductor material of the first photoanode electrode (1) and of the second electrode (7) are independently selected from graphene; carbon nanotubes (CNT); ultra thin metal films; Fluorine doped Tin Oxide (FTO) coated glass; Transparent Conductive Oxides (TCO) and transparent conducting polymers such as Poly(3,4-ethylenedioxythiophene) (PEDOT), Poly(3,4-ethylenedioxythiophene) PEDOT: poly(styrene sulfonate) PSS and Poly(4,4-dioctyl cyclopentadithiophene).

In some examples of these embodiments, the layer of a UV and visible radiation transparent conductor material (1) and of the second electrode (7) are independently selected from graphene; Transparent Conductive Oxides (TCO) and transparent conducting polymers such as Poly(3,4-ethylenedioxythiophene) (PEDOT), Poly(3,4-ethylenedioxythiophene) PEDOT: poly(styrene sulfonate) PSS and Poly(4,4-dioctyl cyclopentadithiophene). Particularly, in some examples, the layer of a UV and visible radiation transparent conductor material (1) and of the second electrode (7) is graphene.

In some embodiments, the first conductive metallic material of the first photoanode electrode (2) and the second conductive metallic material of the second electrode (6) are independently selected from platinum, gold, silver, graphite, aluminum, $TiO_2$, carbon nanotubes, graphene, reduced graphene oxide (rGO), $TiO_2$ doped by Au nanoparticles, Au nanoparticles doped by palladium nanoparticles, $TiO_2$ doped Ag nanoparticles, a semiconductor metal oxide, $TiO_2$/Pt nanoparticles, $TiO_2$/rGO, Pt/Co/$TiO_2$, and mixtures thereof.

In some examples of these embodiments, the first conductive metallic material of the first photoanode electrode (2) is selected from Au nanoparticles, Ag nanoparticles, Pt nanoparticles, $TiO_2$ doped by Au nanoparticles, Au nanoparticles doped by palladium nanoparticles, $TiO_2$ doped by Ag nanoparticles, and mixtures thereof. In particular examples, the first conductive metallic material of the first photoanode electrode (2) is Au nanoparticles.

In some examples of these embodiments, the second conductive metallic material (6) is selected from $TiO_2$, Pt nanoparticles, $TiO_2$ doped by Pt nanoparticles; $TiO_2$/rGO, Pt/Co/TiO$_2$, and mixtures thereof. In particular examples, the second conductive metallic material (6) is TiO$_2$.

In some embodiments of the present invention, the first compartment (A) may comprise the following elements extending from its front end surface to its opposing back end surface (which corresponds with the direction of the incident light), which it is in contact with the polymeric membrane:
1) a first photoanode electrode (A1) which comprises:
   i) optionally, a protective and light-transmissive material (10);
   ii) a layer of a UV and visible radiation transparent conductor material (1); examples of suitable transparent conducting materials are graphene; carbon nanotubes (CNT); ultra thin metal films; Fluorine doped Tin Oxide (FTO) coated glass; Transparent Conductive Oxides (TCO) and transparent conducting polymers such as Poly(3,4-ethylenedioxythiophene) (PEDOT), Poly(3,4-ethylenedioxythiophene) PEDOT: poly(styrene sulfonate) PSS and Poly(4,4-dioctyl cyclopentadithiophene);
   iii) a first conductive metallic material (2), examples of suitable first conductive metallic materials are platinum, gold, silver, graphite, aluminum, TiO$_2$, carbon nanotubes, graphene, reduced graphene oxide (rGO), TiO$_2$ doped by Au nanoparticles, Au nanoparticles doped by palladium nanoparticles, TiO$_2$ doped Ag nanoparticles and mixtures thereof; and
   iv) optionally, one or more of a proton pumping photoactive biological layers (3) comprising oriented purple membrane which contains bacteriorhodopsin protein or any of its genetic variants; stabilized bacteriorhodopsin protein-based sensitizer or any of its genetic variants; or mixtures thereof; the proton pumping photoactive biological layer being deposited on the first conductive metallic material;
2) a water-containing medium (4);
3) a second electrode (A2) which comprises:
   v) optionally, one or more of a proton pumping photoactive biological layers (5) comprising oriented purple membrane which contains bacteriorhodopsin protein or any of its genetic variants; stabilized bacteriorhodopsin protein-based sensitizer or any of its genetic variants; or mixtures thereof;
   vi) a second conductive metallic material (6), examples of suitable second conductive metallic materials are platinum, gold, silver, graphite, aluminum, TiO$_2$, carbon nanotubes, graphene, reduced graphene oxide (rGO), TiO$_2$ doped by Au nanoparticles, Au nanoparticles doped by palladium nanoparticles, and TiO$_2$ doped by Ag nanoparticles, a semiconductor metal oxide, TiO$_2$/Pt nanoparticles, TiO$_2$/rGO, Pt/Co/TiO$_2$, and mixtures thereof; the proton pumping photoactive biological layer being deposited on the second conductive metallic material; and
   vii) a layer of a UV and visible radiation transparent conductor material (7); examples of transparent conducting materials are graphene; carbon nanotubes (CNT); ultra thin metal films; Fluorine doped Tin Oxide (FTO) coated glass; Transparent Conductive Oxides (TCO) and transparent conducting polymers such as Poly(3,4-ethylenedioxythiophene) (PEDOT), Poly(3,4-ethylenedioxythiophene) PEDOT: poly(styrene sulfonate) PSS and Poly(4,4-dioctyl cyclopentadithiophene);
with the proviso that at least one of the proton pumping photoactive biological layers (3) or (5) are present; preferably both of the proton pumping photoactive biological layers (3) and (5) are present.

In the context of the present disclosure, the term "transparent conducting layer" or "layer of a transparent conductor material" and variants, are interchangeable and they refer to a layer of optically transparent and electrically conductive material, wherein optically transparent means that the material allows passing both UV and visible radiation.

In some embodiments, the bio-sensitized photoelectric conversion device is encapsulated in a protective and light-transmissive material or covered by a light-transmissive layer (10). A preferred protective layer is quartz glass, or any structural polymeric material transparent over the entire light spectrum.

In accordance with a preferred embodiment of the present invention, the first photoanode electrode (A1) comprises a first conductive metallic material (2) selected from platinum, gold, silver, graphite, aluminum, TiO$_2$, carbon nanotubes, graphene, reduced graphene oxide (rGO), TiO$_2$ doped by Au nanoparticles, Au nanoparticles doped by palladium nanoparticles, and TiO$_2$ doped Ag nanoparticles and mixtures thereof.

In accordance with an embodiment of the present invention Au may be substituted by Ag, thus resulting in an improvement of the rB absorption range near to UV light (blue), but the catalytic efficiency decrease vs Au.

In accordance with an embodiment of the present invention, Au may be substituted by Pt which provides more catalyst effectiveness, and when the system is producing electricity from hydrogen, the two electrodes of the upper part (first electrode (A1) and second electrode (A2)) can be connected in parallel, thus increasing the H$_2$—electricity conversion efficiency.

In accordance with another embodiment of the present invention, Au may be substituted by TiO$_2$ doped by Au nanoparticles, which changes its absorption range towards the visible (560 nm) by increasing the catalytic activity of the split of the water and allowing the catalysis of the reaction which is produced at the electrode. It also allows UV light to be absorbed by the TiO$_2$ of the second anode electrode.

In accordance with another embodiment of the present invention, Au may be substituted by Au nanoparticles doped by palladium nanoparticles, which increases the catalytic yield of Au, improving the reaction In accordance with an additional embodiment of the present invention, Au may be substituted by TiO$_2$ doped Ag nanoparticles.

In accordance with another preferred embodiment of the present invention, the second electrode (A2) comprises a second conductive metallic material (6) selected from a semiconductor metal oxide, platinum nanoparticles, TiO$_2$, TiO$_2$/Pt nanoparticles, TiO$_2$/rGO, Pt/Co/TiO$_2$, and mixtures thereof.

In accordance with an embodiment of the present invention, TiO$_2$ may be replaced by Pt nanoparticles. Pt nanoparticles provides more catalyst effectiveness, but increase the cost and loss the efficiency in the UV range.

In accordance with another embodiment, TiO$_2$ may be substituted by TiO$_2$/Pt nanoparticles. This configuration improves catalysis, efficiency to split water but increases the cost.

In accordance with an embodiment of the present invention, $TiO_2$ may be substituted by $TiO_2$/rGO. With this configuration, the photocurrent may be increased up to 9 times.

In accordance with another embodiment of the present invention, $TiO_2$ may be substituted by Pt/Co/$TiO_2$. This triple alloy may be used to improve the catalytic activity of Pt and $TiO_2$ and the electronic flow through the graphene by electromagnetic activity.

In accordance with an embodiment of the present invention, nanoparticles of the conductive material or carbon nanotubes decorated with said nanoparticles may be applied. Using nanotubes improves the conductivity of electrons but reduces catalytic performance.

The polymeric membrane (C) is selected between those known polymeric membranes which allow the passage of protons. A suitable example of polymeric membrane for use in the device of the present invention is, but not limited to Nafion.

In some embodiments, the second compartment (B) may comprise the following elements extending from its front end surface which it is in contact with the polymeric membrane to its opposing back end surface:
i) optionally, a layer of a UV and visible radiation transparent conductor material (8); examples of transparent conductor materials are graphene; carbon nanotubes (CNT); ultra thin metal films; Fluorine doped Tin Oxide (FTO) coated glass; Transparent Conductive Oxides (TCO) and transparent conducting polymers such as Poly(3,4-ethylenedioxythiophene) (PEDOT), Poly(3,4-ethylenedioxythiophene) PEDOT: poly(styrene sulfonate) PSS and Poly(4,4-dioctyl cyclopentadithiophene);
ii) a third conductive metallic material (9) selected from platinum, gold, silver, graphite, aluminum, $TiO_2$, carbon nanotubes, graphene, reduced graphene oxide (rGO), $TiO_2$ doped by Au nanoparticles, Au nanoparticles doped by palladium nanoparticles, $TiO_2$ doped by Pt nanoparticles, $TiO_2$/rGO, Pt/Co/$TiO_2$, and $TiO_2$ doped by Ag nanoparticles and mixtures thereof; the third conductive metallic material working as a cathodic electrode; and optionally
iii) an hydrogen collecting deposit (B2).

In accordance with an embodiment of the present invention, the third conductive metallic material (9) is selected from a semiconductor metal oxide, platinum nanoparticles, $TiO_2$, $TiO_2$ doped by Pt nanoparticles, $TiO_2$/rGO, Pt/Co/$TiO_2$, and mixtures thereof.

Deposition of the third conductive metallic material (9) of compartment (B) onto the polymeric membrane (C) may be performed by any of the known methods described in the art.

In some embodiments, a layer of a UV and visible radiation transparent conductor material (8) may be previously deposited, preferably by chemical vapor deposition, onto the polymeric membrane (C) surface to improve the conductivity of the membrane and then, the third conductive metallic material (9) is deposited onto the transparent conductor material layer (8) by e.g electrodeposition.

The one or more of a proton pumping photoactive biological layers comprising oriented purple membrane (3, 5) which contains bacteriorhodopsin protein or any of its genetic variants; stabilized bacteriorhodopsin protein-based sensitizer or any of its genetic variants; or mixtures thereof; may be deposited on the surface of the first and second conductive metallic materials by a number of methods known in the art. In some embodiments, the proton pumping photoactive biological layers may be generated either by using electrophoretic deposition or by electrostatic layer-by-layer deposition.

In accordance with a particular embodiment of the present invention, proton pumping photoactive biological layers are deposited by electrostatic layer-by-layer deposition.

Figure 4:
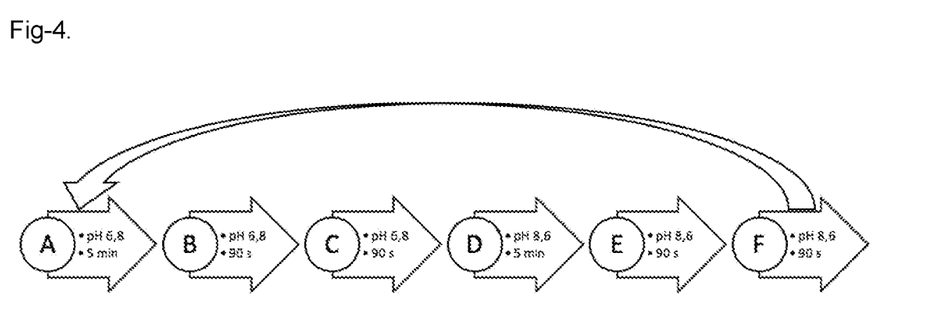
FIG. 4 represent the sequence of tanks used in the lyer-by-lyer method.

The layer by layer deposition method to deposit the protein on a substrate comprises to submerge the substrate in a sequence of tanks containing suitable materials for a defined period of time (see FIG. 4):

Start with tank A to tank F (note that between process C and D there is a drying time, which may be from 5-10 minutes, preferably 7 minutes; and the same case between processes F and A). The process is cyclic, so that at the end of the deposit F starts again with the A. One cycle results in depositing one layer of protein on the substrate.

The materials of each of the deposits are as follows:
Tank A: Poly (diallyl dimethylammonium) chloride, PDDA, Mw: 10,000-20,000, which was dissolved in 20 mmol L-1 in milli-Q Water (pH 6.8).
Tanks B and C: Water milli-Q at 6.8 pH
Tank D: The PM (Purple membrane=Br) was used at a concentration of 0.5 mg/ml of bR and the pH was adjusted to 8.6 using 0.1M NaOH before each experiment
Tanks E and F: water milli-Q at 8.6 pH using 0.1M NaOH before each experiment.

In some embodiments of the present invention, construction of the first photoanode electrode (A1) of the first compartment (A) comprises the following steps:
i) depositing a layer of a UV and visible radiation transparent conductor material (1) on the surface of a protective and light-transmissive material (10); preferably deposition is made by chemical vapor deposition;
ii) electrodeposition of the first conductive metallic material (2) onto the transparent conductor material layer (1); and
iii) depositing the one or more proton pumping photoactive biological layers (3) onto the first conductive metallic material (2).

In some examples of the present invention, the protective and light-transmissive material (10) is selected from quartz-glass and any structural polymeric material transparent over the entire light spectrum;

In some embodiments of the present invention, construction of the second electrode (A2) of the first compartment (A) comprises the following steps:
i) depositing a layer of a UV and visible radiation transparent conductor material (7) on the polymeric membrane (C) surface;
ii) depositing the second conductive metallic material (6); preferably deposition is made by chemical vapor deposition; onto the UV and visible radiation transparent conductor material (7); and
iii) optionally, depositing the one or more proton pumping photoactive biological layers (5) on the second conductive metallic material (6).

In some examples of the present invention, the water-containing medium (4) may be formed of a substantially UV and visible radiation transparent substance capable of conducting hole charge carriers. In some examples, the water-containing medium may be one of a solid, liquid, or gel electrolytic material that is optically transmissive, with a low conductivity, and able to provide protons. In accordance with an embodiment of the present invention, milli-pure/milli-Q water may be used as the water-containing medium (4).

In some other examples, the water-conductive medium (4) is a electrolytic aqueous solution containing, preferably 0.01 to 5 M, more preferably from 0.1 to 2 M of a supporting salt. Examples of the supporting salts are those of the formula $M_mX_n$ in which: M may be selected from magnesium, calcium, lithium, potassium and sodium; X may be selected from anions of weak or strong acids selected from carbonates, bicarbonates, sulfates, hydroxides and halides. In some of these cases, the supporting salt may be selected from $NaHCO_3$, $NaCO_2CH_3$, $KHCO_3$, $K_2CO_3$, $Na_2SO_4$, $K_2SO_4$, KCl and $KClO_4$. The pH value of the electrolytic aqueous solution is preferably around the neutral value, that is, preferably 5 to 10, more preferably 6 to 9.

In another examples, the water-conductive medium (4) is a solid electrolyte. Examples of solid electrolytes preferably used in the present invention include yttria-stabilized zirconia, beta-alumina solid electrolyte, lanthanum trifluoride, silver iodide, copper(I) iodide, rubidium silver iodide ($RbAgI_2$), $Ag_2HgI_4$. and polymer electrolytes prepared by introducing a salt as an ion carrier into a polymer medium such as gelatin, agar, polyvinyl alcohol and commonly employed cation exchange resins and anion exchange resins.

In particular examples, the water-conductive medium (4) comprise a chloride salt, preferably KCl in a concentration in the range of 50 mM to 0.1 M KCl.

The amount of water-conductive medium (4) may be determined by the amount of oxygen that is generated. The chemical balance must be maintained $$4OH^-\rightarrow 4e^-+2H_2O+O_2$$

If the concentration of $O_2$ increases, the equilibrium tends to the left.

The reversible bio sensitized photoelectric conversion and $H_2$ to electricity conversion device herein described takes advantage of most of the range of UV-visible light. This way it can achieve greater performance in adverse weather conditions. The system is closed, thus it avoid the water supply and avoid a conventional PEMFC to take advantage of $H_2$. The reversible bio sensitized photoelectric conversion and $H_2$ to electricity conversion device herein described is capable of producing energy at the same time as hydrogen and is reversible, being able to store this hydrogen and become again electric energy in the same system without need of an additional system.

Furthermore, the reversible bio sensitized photoelectric conversion and $H_2$ to electricity conversion device of the present invention shows a higher efficiency (higher than 17%) than known systems based on rhodopsin.

The direct operation mode of the system is based on the imbalance that the protein causes in the water. The protein, when receiving sunlight from the part of the solar spectrum, displaces the free protons. In the environment, a pH gradient is generated up to 4 units and causes the water balance to shift to the right:

$$2H_2O\rightarrow H_3O^++OH^-$$

This imbalance in the presence of catalysts such as Au, Ag or Pt at the anode and Pt, $TiO_2$ and rGO at the cathode promote reactions that facilitate the displacement of electrons.

In basic environment catalyzed with gold, it occurs:

$$4OH^-\rightarrow 4e^-+2H_2O+O_2$$

In acid environment at the cathode is produced:

$$4H^++4e^-\rightarrow 2H_2(gas)$$

In accordance with some embodiments, the system may operate in the reverse mode. That occurs when the protein stops receiving energy from the photons, it stops pumping protons. The $H_2$ formed, catalyzed by the presence of Pt in the cathode tends to oxidize $$2H_2\rightarrow 4H^++4e^-$$

And the oxygen present in the water tends to be reduced in the presence of $Pt/TiO_2$ generating an inverse current $$4e^-+4H^++O_2\rightarrow 2H_2O$$

FIG. 1 represent a side section of the bio sensitized photoelectric conversion device of the present invention.

The reactions occurring in direct operation mode are:
In part A:

$$4H_2O\rightarrow 4H^++4OH^-$$

$$4OH^-\rightarrow 4e^-+2H_2O+O_2$$

In part B:

$$H_2\rightarrow 2e^-+2H^+$$

$E=3.6$ Vdc

Whereas the reactions occurring in reverse mode are:
In part B:

$$H_2\rightarrow 2H^++2e^-$$

In part A:

$$2e^-+2H^++\tfrac{1}{2}O_2\rightarrow H_2O$$

$E=0.9$ Vdc

Thus, in accordance with some embodiments of the present invention, the system is activated when it receives photons from the solar irradiation, both visible and UV part of the light spectrum. Upon receiving photons, bR generates a proton gradient across the polymeric membrane. The proton transport mechanism of bR is facilitated by absorption of light in the 500-650 nm wavelength region. Upon absorption of light, the protein undergoes a number of conformational changes resulting in proton translocation. These protons pass to part (B) of the system, thanks to the polymeric membrane (C), causing the electrons in part (A) to pass also to part (B) through the electrodes and generating $H_2$.

The bR transforms the received photons into a proton pump with the following cadence: 1 photon-1 proton each 8-12 ms (photocycle depends on different mutant variant).

When the system operates in the reverse mode, the hydrogen formed during the direct mode and storaged in the hydrogen collecting deposit (B2), is again separated into protons and electrons. Thanks to the electronics of the system, electrons return from part (B) to part (A) through the electrodes, causing the protons through the membrane also to return to part (A).

The electronic of the system is connected as follows:
In direct mode:
i) A1 is connected to B1 and
ii) A2 is connected to B1
In reverse mode:
i) B1 is connected to A2

The connexions are fixed, and depending of the mode, direct or reverse, the switch allows the pass of the electricity of A1 to B1 and simultaneously A2 to B1 in direct mode or allows the pass of the electricity from B1 to A2 in reverse mode.

The switch also is open when there is overpotential or overpression for security of the system.

Thus, in accordance with some embodiments of the present invention, the system operates in the reverse mode, i.e. when no radiation is directed onto the first photoanode electrode (A1) of the first compartment (A). In the reverse mode, the $H_2$, which has been formed when radiation strikes and has been stored in the hydrogen collecting deposit (B2), is reduced by the third conductive metallic material (9) present in the third electrode, causing the protons passing through the membrane and return from part B to part A, and together with the oxygen present in the media (in part A) tends to form water in the presence of the second conductive metallic material (7) generating an inverse current.

This ensures that the system is completely closed and reversible.

In some examples, when the device is in use, both the bR and the second conductive metallic material (6) of the second electrode (e.g. $TiO_2$) are working as photoreceptors. The bR absorbs in the light range of the visible spectrum, while the second conductive metallic material (6) absorbs in the UV range.

In the direct mode of operation, the second conductive metallic material (6) performs the photocatalyst function in aqueous environment when it receives photons above the 3.2 eV (388 mm) band causing:

$$TiO_2 + hv \rightarrow h^+ + e^-$$

$$H_2O + h^+ \rightarrow OH^- + H^+$$

The polymeric membrane (C) is used as a proton membrane to separate the protons from the medium as hydrogen is formed.

In accordance with an embodiment of the present invention, the polymeric membrane (C) is characterized by transferring protons through itself. In accordance with an embodiment of the present invention, the polymeric membrane (C) may comprise, deposited onto at least one of its surfaces, a layer of a UV and visible radiation transparent conductor material to improve the conductivity of the membrane; in accordance with a preferred embodiment, the polymeric membrane comprises deposited a layer of a UV and visible radiation transparent conductor material onto both of its surfaces. More preferred, the polymeric membrane comprises graphene layer deposited onto both of its surfaces.

Thus, in accordance with an embodiment of the present invention, the polymeric membrane (C) comprises a graphene layer (7) deposited onto one of its surfaces and onto the graphene layer (7) it is deposited the second conductive metallic material (6) of the second anode electrode; whereas onto the other side of the polymeric membrane, also a graphene layer (8) is deposited thereon and onto that graphene layer (8) it is deposited the third conductive metallic material (9).

In accordance with an embodiment of the present invention, only one graphene layer is deposited onto the polymeric membrane, onto the side oriented to the second electrode (A2) or alternatively onto the side oriented to the third electrode (B1).

In accordance with another embodiment of the present invention, both the second conductive metallic material (6) of the second electrode and the third conductive metallic material (9) of the cathode electrode are directly deposited onto the polymeric membrane.

In accordance with an embodiment of the present invention, the photoanode electrode (A1) of the first compartment comprises a first conductive metallic material (2) content from 0.02 $mg/cm^2$ to 5 $mg/cm^2$, from 0.2 $mg/cm^2$ to 5 $mg/cm^{2-}$; from 0.14 $mg/cm^2$ to 1 $mg/cm^2$, from 0.4 $mg/cm^2$ to 1 $mg/cm^2$, from 0.4 $mg/cm^2$ to 0.8 $mg/cm^2$, or from 0.6 $mg/cm^2$ to 0.8 $mg/cm^2$.

In accordance with an embodiment of the present invention, the second electrode (A2) of the first compartment comprises a second conductive metallic material (6) content from 0.01 $mg/cm^2$ to 5 $mg/cm^{2-}$; in some particular embodiments the content is comprised from 0.05 $mg/cm^2$ to 4 $mg/cm^2$. In accordance with some embodiments, the content is comprised from 0.1 $mg/cm^2$ to 3 $mg/cm^{2-}$; in additional embodiments, the content is comprised from 0.5 $mg/cm^2$ to 2 $mg/cm^2$. In some other embodiments, the content is comprised from 1 $mg/cm^2$ to 4 $mg/cm^2$, more preferably from 2 $mg/cm^2$ to 3 $mg/cm^2$.

In accordance with an embodiment of the present invention, the third electrode (B1) of the second compartment (B) comprises a third conductive metallic material (9) content from 0.02 $mg/cm^2$ to 5 $mg/cm^2$, from 0.2 $mg/cm^2$ to 5 $mg/cm^{2-}$; from 0.1 $mg/cm^2$ to 1 $mg/cm^2$, or from 0.3 $mg/cm^2$ to 1 $mg/cm^2$.

A polymeric membrane with the following catalyst amounts may be used:
0.3 $mg/cm^2$ PtC (40%)
3 $mg/cm^2$ $TiO_2$ nano, 21 nm max size (TEM) trace materials ≥99.5%

In accordance with a preferred embodiment, the UV and visible radiation transparent conductor material is graphene; suitable graphene layer deposited onto the polymeric membrane and onto the first conductive metallic material of the photoanode electrode present in the first compartment (A) may have a resistivity from $10^{-4}$ Ωcm to $10^{-6}$ Ωcm, preferably $10^{-5}$ Ωcm. The transmittance of the graphene layer may be preferably from 90% to 99%, preferably 98%.

In accordance with a particular embodiment of the present invention, the protective and light-transmissive material (10) is quartz glass and the layer of a UV and visible radiation transparent conductor material (1) is CVD graphene with a resistivity of $10^{-5}$ Ωcm and 97% transmittance.

In some examples, for the construction of the first electrode (A1), electrodeposition of Au nanoparticles on the substrate may be performed, being the substrate a quartz-CVD graphene part as described above. In accordance with some examples, the electrodeposition of Au nanoparticles on the substrate may result in a uniform layer of between 0.3 to 1.0 $mg/cm^2$, preferably between 0.4 to 0.8 $mg/cm^2$, being particularly preferred 0.6 $mg/cm^2$ of nanoAu particles (size between 2.5-7 nm).

In accordance with an embodiment of the present invention, between 100-400 layers of bR are deposited onto the first conductive metallic material (1), preferably 120-300 layers, more preferably between 130-200 layers, being particularly preferably 150 layers.

In accordance with an embodiment of the present invention, between 100-400 layers, preferably 120-300 layers, more preferably between 150-250 layers, being particularly preferably 200 layers of bR are deposited onto the second conductive metallic material (6).

Bacteriorhodopsin exists in highly concentrated clusters termed purple membrane. Within these clusters the concentration of bR is roughly 75%. This protein clusters, embedded in their native lipid matrix can be isolated very effectively through lysis of the bacterial cells followed by differential centrifugation to remove all other cellular debris. Then resulting in highly pure and stable purple membrane fragments. The skilled person knows the methods and conditions to perform such a processes, e.g. those described in US2009142852, which it is herein incorporated by reference.

In accordance with some preferred embodiments, the proton pumping photoactive biological layer comprises oriented purple membrane.

In accordance with other embodiments, the proton pumping photoactive biological layer comprises bacteriorhodopsin genetic variants (mutants) in order to achieve the correct orientation and good adhesion of the bR layers. The skilled person in the art may know different bR mutants that enhance packing, orientation, thermodynamic, adhesion and combinations thereof. Accordingly, bR mutants having particular characteristics useful for the generation of solar energy are known in the art. Thus, there are known in the art mutants having the ability to pump chloride anions for brine splitting; having enhanced ability to covalently attach to metal surfaces and metal-coated particles; or mutants having enhanced the formation of orientated layers in such a way as to increase packing.

In accordance with an embodiment of the present invention, the proton pumping photoactive biological layer comprises a bacteriorhodopsin genetic variant wherein one or more aminoacids of the amino acid sequence in the bacteriorhodopsin protein are replaced with one or more aminoacids that are different from that of the wild type $H.$ $salinarum$ bacteriorhodopsin protein.

In some embodiments, the proton pumping photoactive biological layer comprises a bacteriorhodopsin genetic variant wherein one or more aminoacids of the amino acid sequence in the bacteriorhodopsin protein to the loops that are in the intracellular part are replaced with one or more cysteine aminoacids.

Thus, mutants most attuned to Au are anyone who changes an amino acid by a cysteine to the loops that are in the intracellular part. In some embodiments of the present invention, the following known mutants may be used V101C, M163C, A160C, T247C and E166C, obtaining similar results at the photocycle level (cycle between pumping and proton pumping) and in orientation.

In some embodiments, the proton pumping photoactive biological layer comprises a bacteriorhodopsin genetic variant wherein one or more glutamic acid of the amino acid sequence in the bacteriorhodopsin protein to the loops that are in the extracellular part are replaced with one or more glutamine aminoacid.

Mutants most attuned to $TiO_2$ are anyone who changes a glutamic acid to a glutamine from the loops of the extracellular part. In some embodiments, the following known mutants may be used in order to adhere the proteins and ensure orientation and anchorage: E74Q, E194Q, and double mutant E194Q/E204Q.

In the above lists of bR mutants, the first letter in each member represents the one letter code for the amino acid that is at that position in the native bR of $H.$ $salinarum$; the number represents the position of the amino acid starting from the N-terminus (excluding the leader peptide); and the second letter represents the one letter code for the amino acid that is different from the amino acid in the native bR.

The one or more of a proton pumping photoactive biological layers comprising oriented purple membrane which contains bacteriorhodopsin protein or any of its genetic variants; stabilized bacteriorhodopsin protein-based sensitizer or any of its genetic variants; or mixtures thereof; may be placed onto surfaces using known methods in the art, examples of those methods include, but not limited are electrospray deposition, use of polyhistidine-tags, affinity chromatography, use of antibodies against bR and electrostatic layer-by-layer methods.

In accordance with an embodiment of the present invention, the system is used in the direct operation mode for generating electricity by exposing the system to sunlight, which causes the bR to pump protons, causing a large potential difference that is used to generate and electrical current. Thus, in accordance with this embodiment of the present invention, the system is used in a method for generating energy by water splitting, producing oxygen gas at the anode and hydrogen gas at the cathode; the hydrogen gas may be collected, and used as an energy source when the system operates in the reverse mode. Production of energy and hydrogen may be done sequentially or simultaneously.

To store the hydrogen, an inert gas, preferably argon may be used to compensate for the pressure of the upper system and the pressure of the lower system. The inert gas, when is mixed with $H_2$, reduces the risk of explosion. In addition, its weight than the $H_2$ weight, thus it keeps the $H_2$ at the top closest to the Pt.

For the realization of the connectors, 3 copper frames may be used. The thickness may range from 0.05 to 0.3 mm, preferably 0.1 mm thickness.

The system may be sealed with special silicone to prevent $H_2O$ from coming in contact with copper; and prevent $O_2$, $H_2$ and Ar from escaping.

The connector of the first conductive metallic material (1) layer and that of the second conductive metallic material (6) may be connected through a diode and a switch. And also, the connector of the second conductive metallic material (6) and that of the third conductive metallic material (9) may be connected through a diode and a switch.

In accordance with another embodiment of the present invention, it provides a system with operates in alternating current.

Using the system in alternating allows avoiding adding additional deposits of gases and avoiding inverters.

When the system operates in alternating current, in an $H_2O$ environment under atmospheric pressure, rB, when activated by photons (in the visible light stream), shifts the water balance to $$H_2O \rightarrow H^+ + OH^-$$

by the pumping effect of the protons and creates a pH gradient of between 1-4. This causes the environment to become basic, because of the large amount of $OH^-$ present.

The first conductive metallic material (1) catalyzes the reaction $$4OH^- \rightarrow 4e^- + 2H_2O + O_2$$

and yields electrons that pass through the layer of a UV and visible radiation transparent conductor material (1) and are transported to the other side of the polymeric membrane (C), where there are the protons that demand electrons.

The second conductive metallic material (6) also catalyzes the reaction $$4OH^- \rightarrow 4e^- + 2H_2O + O_2$$

and the bR (if present) pumps the protons to the other side of the polymeric membrane (C) by the demand of electrons of the protons.

As a result, the system generates $O_2$ and consumes $H_2O$ to the extent that the presence of $H_2O$ decreases, and the partial pressure of the oxygen increases so that the equilibrium shifts towards the other direction $$H_2O + O_2 + 4e^- \rightarrow 4OH^-$$

This causes an attraction to the electrons displaced towards the other side of the polymeric membrane, causing them to return and creating in this way an inverse current until the reaction returns to move in reverse, creating of this form, an alternating current.

When the system operates in alternating current, it facilitates the management of the equilibrium of the reaction $$4OH^+ \rightarrow O_2 + 2H_2O + 4e^-$$

always maintaining an imbalance in the system, it reduces the energy collection since when the system is in operation (reverse), solar energy is not usable. The AC system, reduces costs of electronic complements as investors. Conventional solar modules generate CC electricity that must be converted to AC electricity so that it can be used in houses or other buildings. The present invention allows avoiding the cost associated to this conversion.

In accordance with an embodiment of the present invention, it provides a system which is transparent. Making the system transparent involves two main advantages:
1. light that is not absorbed by the module may be absorbed by a conventional silicon module and may therefore overlap and increase efficiency per m$^2$;
2. the system may capture sunlight from both directions, thus taking advantage of indirect light, or if installed in a window, take advantage of the light inside and outside.

For this purpose, 2D CVD graphene (97% light-transmissive) may be preferably used, on both sides of the polymeric membrane, i.e. as the layer of a UV and visible radiation transparent conductor material layers (7) and (8), which may serve as a substitute for graphite.

In addition to being light-transmissive, graphene CVD generates another improvement in the system, and is that it does not let gases like $H_2$ or $O_2$ are transferred through the layer of graphene. In this way, life is extended to the polymeric membrane, being one of the most important critical points in the life cycle of the system.

In accordance with an embodiment of the present invention, the deposition of the second conductive metallic material (6), preferably $TiO_2$ or PtC nanoparticles, may be performed by electrospray, generating a uniform layer. Nanoparticles may preferably have a thickness lower than 50 nm, more preferably lower than 30 nm, being particularly preferred when the thickness is lower than 20 nm.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

Reference signs related to drawings and placed in parentheses in a claim, are solely for attempting to increase the intelligibility of the claim, and shall not be construed as limiting the scope of the claim.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1

Construction Module 5 cm×5 cm
Construction Part A:
1. Prepare the Substrate Quartz Glass/Graphene/nanoAu/Br A quartz glass+ CVD graphene 7 cm×7 cm purchase with 97% transmittance, was used as the upper part of the system.

For the construction of the first electrode, an electrode-position of Au nanoparticles was performed on the substrate (Quartz-graphene) in 5 cm×5 cm of the total surface, obtaining an uniform layer of 0.6 mg/cm$^2$ of nanoAu particles (size between 2.5-7 nm). The resistivity was checked with tester achieving $10^{-5}$ Ωcm.

150 layers of bR T247C were added to the Au/graphene/Quarzo substrate by the layer by layer method using the robot and the Quarzo part It was covered with a film to prevent the protein from being adhered.

bR T247C mutant was previously described in J. Phys. Chem. C 2014, 118, 16710-16717.

2. Prepare the Substrate bR/TiO$_2$/Graphene/Nafion®/Graphene/Pt

Nafion® membrane was used as a proton membrane to separate the protons from the medium as hydrogen is formed. A membrane 7 cm×7 cm was purchased and contains a monolayer Graphene in both parts with 97% transmittance.

The following catalyst amounts was added with electrospray process on the 5 cm×5 cm of the total surface: 0.3 mg/cm$^2$ PtC (40%), and in the other hand 3 mg/cm$^2$ TiO$_2$ nano, 21 nm max size (TEM) trace materials 99.5% The resistivity was checked with tester achieving $10^{-5}$ 0 cm in the both parts.

200 layers of bR E194Q/E204Q were added to the TiO$_2$ part substrate by the layer by layer method using the robot and the Pt part It was covered with a film to prevent the protein from being adhered.

bR E194Q/E204Q double mutant was previously described in Biophysical Journal Volume 2004, 86:1673-1681.

3. Assembly Both Substrates and Placement the Cu Connectors.

3 Cu frames 7 cm×7 cm×0.1 cm and 1 cm of width were used as connectors and were attached on the 3 graphene parts of the three electrodes with the aid of adhesive tape.

Special silicone was used to seal the two substrates. It was first applied to the Quarz/Graphene/Au/Protein substrate. 30 ml of water mili-q was used to maintain the proteins and to provide protons to the medium, this was placed on the substrate Quarz/Graphene/Au/Protein. Finally by vacuum and the special silicone was sealed next to the other substrate Protein/TiO$_2$/Graphene/Nafion®/Graphene/Pt.

Construction PART B and Assembly to PART A:

This part stores the H$_2$ generated by the system, was comprised of a polycarbonate plate 7 cm×7 cm 1 cm thick. In this case a rubber frame of 7 cm×7 cm×0.5 cm and 2 cm of amplitude was used as a joint and was sealed with special silicone to the polycarbonate. To seal the part A with the part B uses special silicone and was realized in an atmosphere of argon to avoid that the gas that was stored initially was oxygen.

Finally cables were connected and soldered to the Cu frames in order to be able to perform Voltage and intensity measurements using Voltammeter.

Figure 2:
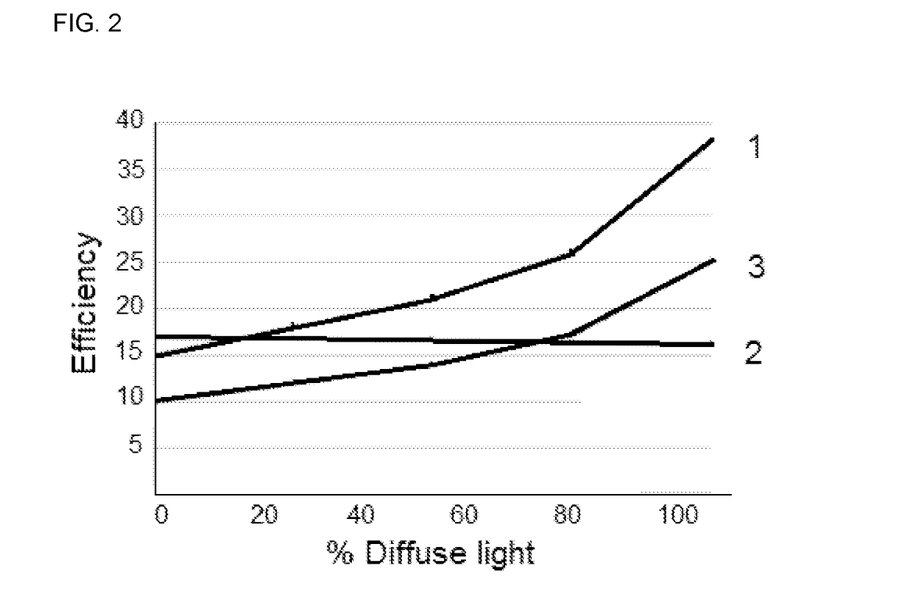
FIG. 2 shows a comparison of the energy of the device of the present invention provided in different combinations of direct irradiation versus diffuse irradiation was performed. Efficiency vs. direct/diffuse spectrum of the device of the invention (1), a silicon poly-crystalline (2) and the device of the invention without $H_2$ (3)

FIG. 2 shows a comparison of the energy that the module of the present disclosure provided in different combinations of direct irradiation versus diffuse irradiation was performed.

For this purpose, a spectrophotometer was used, which provided a power of 10 W over the 100 cm² of the prototype. To the lamp was added a filter that allowed providing the power following the light spectrum of the direct light and the one of the diffuse light.

The results were compared vs. a polycrystalline silicon module to see its behavior vs. that of the module of the disclosure.

The graphic shows that as the light spectrum becomes more diffuse for the same power, the module of the present disclosure achieves up to 2.5 times more efficiency.

This phenomenon occurs because the lithic spectrum, when it is more diffuse, acquires the composition shown in the following graph. Moving the whole area of the lithic spectrum towards the part closest to the UV that is the range of light where the module has greater absorption.

These diffuse light conditions occur on cloudy days, rain or high pollution areas. This reason means that conventional modules cannot be installed in areas with adverse weather conditions as their cost cannot be amortized.

Figure 3:
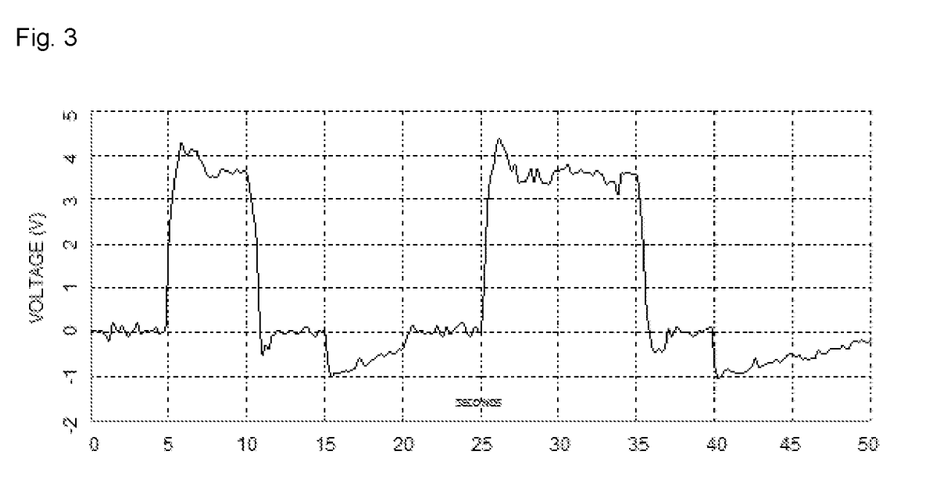
FIG. 3 shows the voltage generated (measured by voltammeter) by the device of the present invention when working in sunlight (direct operation mode) and without it (reverse mode).

FIG. 3 shows the voltage generated (measured by voltammeter) by the system when working in sunlight and without it. It is observed how the system is generating hydrogen, and how it is being consumed at the moment the electronics is in reverse mode. It is observed that the potential decreases as the hydrogen is being consumed.
Second 0-5: Turn off light (direct electronic)
Second 5-10: Turn on light (direct electronic)
Second 10-15: Switch off/Turn light off (reverse electronic)
Second 15-20: Switch on/Turn light off (reverse electronic)
Second 20-25: Switch off/Turn light off (direct electronic)
Second 25-35: Turn on light (direct electronic)
Second 35-40: Switch off/Turn light off (reverse electronic)
Second 40-50: Switch on/Turn light off (reverse electronic)

The graph shows the potentials generated in (+) when the protein is pumping protons. In this case, the system tends to split the water and generates $O_2$(gas) and $H_2$(gas).

When the system operates in a different direction, the presence of pure $O_2$(gas) (without $N_2$) increases the efficiency of the reaction $$4H^+ + 4e^- + O_2 \rightarrow 2H_2O$$

Up to 3 times more than in a conventional cell, so an excess of $O_2$ above 5% is not necessary.

When the system works in this direction (return $4H^+ + 4e^- + O_2 \rightarrow 2H_2O$) the reaction releases heat, set the working temperature at 60° C. This facilitates that the system can be installed in colder areas where the heat can be harnessed for heating and keep the system above 0° C.

The system is capable of storing hydrogen. Of the total energy produced, approximately 50% is converted to Hydrogen. Hydrogen is converted into electric current (55% aprox) at times when there is no sunlight, and provides heat (45% aprox).

The system generates more than twice as much efficiency in diffused light conditions as conventional photovoltaic modules.

The pH gradient performed by the protein of up to 4 pH units maintains the upper part that touches the gold at pH=9, facilitating that the presence of OH⁻ is higher and in the part of $TiO_2$ at pH=5, potentiating in these conditions (acid environment) a greater proton production of $TiO_2$. In addition, the protein quickly pumped the free protons making it difficult for the electrons to re-generate less H—H bonds and thus favoring the increase in voltage.

Protons, being rapidly displaced by bR, prevent the formation of superoxidant ions such as $O_{2-}$ and OH⁻ produced by $TiO_2$.

REFERENCES CITED IN THE APPLICATION

1. J Nanoscience and Nanotech, 2009, 9, 1679-1687
2. U.S. Pat. No. 9,023,989
3. Proc Natl Acad Sci USA, 1981. 78(11) 6744-6748
4. Gene, 1990. 96(1) 125-128
5. Biotechniques, 1994. 16(5) 820-823.
6. US2009142852
7. Biophysical Journal Volume 2004, 86:1673-1681
8. J. Phys. Chem. C 2014, 118, 16710-16717
9. Adv. Colloid and Interface Sci. 2015, 225: 194-202

The invention claimed is:

1. A reversible bio sensitized photoelectric conversion and $H_2$ to electricity conversion device comprising a first compartment (A) and a second compartment (B); the first compartment (A) comprises a first photoanode electrode (A1) and a second electrode (A2) with a water-containing medium (4) therebetween; wherein a polymeric membrane (C) is disposed between the first compartment (A) and the second compartment (B); the second compartment (B) comprises a third electrode (B1), and a hydrogen collecting deposit (B2);

wherein
the first compartment (A), extending from its front end surface to its opposing back end surface, comprises:
  i.1 the first photoanode electrode (A1) which comprises:
    i.1.1 a layer of a visible or UV and visible radiation transparent conductor material (1);
    i.1.2 a first conductive metallic material (2); and
    i.1.3 optionally, one or more of a proton pumping photoactive biological layers (3) comprising oriented purple membrane containing bacteriorhodopsin protein or any of its genetic variants; stabilized bacteriorhodopsin protein-based sensitizer or any of its genetic variants; or mixtures thereof;
  the one or more proton pumping photoactive biological layers (3) being deposited on the first conductive metallic material (2);
  i.2 the water-containing medium (4);
  i.3 the second electrode (A2) which comprises:
    i.3.1 optionally, one or more of a proton pumping photoactive biological layers (5) comprising oriented purple membrane containing bacteriorhodopsin protein or any of its genetic variants; stabilized bacteriorhodopsin protein-based sensitizer or any of its genetic variants; or mixtures thereof; and
    i.3.2 a second conductive metallic material (6);
  the one or more proton pumping photoactive biological layers (5) being deposited on the second conductive metallic material (6); and
    i.3.3 a layer of a visible or UV and visible radiation transparent conductor material (7);
  with the proviso that at least one of the proton pumping photoactive biological layers (3) or (5) is present.

2. The device according to claim 1, wherein the layer of a visible or UV and visible transparent conductor material of the first photoanode electrode (1) and of the second electrode (7) are independently selected from graphene; carbon nanotubes (CNT); ultra thin metal films; Fluorine doped Tin Oxide (FTO) coated glass; Transparent Conductive Oxides (TCO); transparent conducting polymers; Poly(3,4-ethylenedioxythiophene) (PEDOT); Poly(3,4-ethylenedioxythiophene) PEDOT: poly(styrene sulfonate) PSS; and Poly(4,4-dioctyl cyclopentadithiophene).

3. The device according to claim 1, wherein the first conductive metallic material of the first photoanode electrode (2) and the second conductive metallic material of the second electrode (6) are independently selected from platinum, gold, silver, graphite, aluminum, $TiO_2$, carbon nanotubes, graphene, reduced graphene oxide (rGO), $TiO_2$ doped by Au nanoparticles, Au nanoparticles doped by palladium nanoparticles, $TiO_2$ doped by Ag nanoparticles, a semiconductor metal oxide, $TiO_2$/Pt nanoparticles, $TiO_2$/rGO, Pt/Co/$TiO_2$, and mixtures thereof.

4. The device according to claim 1, wherein the first compartment (A) comprise the following elements extending from its front end surface to its opposing back end surface, which it is in contact with the polymeric membrane:
1) the first photoanode electrode (A1) which comprises:
   i) optionally, a protective and light-transmissive material (10);
   ii) the layer of a visible or UV and visible radiation transparent conductor material (1) selected from graphene; carbon nanotubes (CNT); ultra thin metal films; Fluorine doped Tin Oxide (FTO) coated glass; Transparent Conductive Oxides (TCO); transparent conducting polymers; Poly(3,4-ethylenedioxythiophene) (PEDOT; Poly(3,4-ethylenedioxythiophene) PEDOT: poly(styrene sulfonate) PSS; and Poly(4,4-dioctyl cyclopentadithiophene);
   iii) the first conductive metallic material (2) selected from platinum, gold, silver, graphite, aluminum, $TiO_2$, carbon nanotubes, graphene, reduced graphene oxide (rGO), $TiO_2$ doped by Au nanoparticles, Au nanoparticles doped by palladium nanoparticles, $TiO_2$ doped Ag nanoparticles and mixtures thereof; and
   iv) the one or more of a proton pumping photoactive biological layers (3) comprising oriented purple membrane containing bacteriorhodopsin protein or any of its genetic variants; stabilized bacteriorhodopsin protein-based sensitizer or any of its genetic variants; or mixtures thereof; the one or more proton pumping photoactive biological layers being deposited on the first conductive metallic material;
2) the water-containing medium (4);
3) the second electrode (A2) which comprises:
   v) the one or more of a proton pumping photoactive biological layers (5) comprising oriented purple membrane containing bacteriorhodopsin protein or any of its genetic variants; stabilized bacteriorhodopsin protein-based sensitizer or any of its genetic variants; or mixtures thereof;
   vi) the second conductive metallic material (6) selected from platinum, gold, silver, graphite, aluminium, $TiO_2$, carbon nanotubes, graphene, reduced graphene oxide (rGO), $TiO_2$ doped by Au nanoparticles, Au nanoparticles doped by palladium nanoparticles, $TiO_2$ doped by Ag nanoparticles, a semiconductor metal oxide, $TiO_2$/Pt nanoparticles, $TiO_2$/rGO, Pt/Co/$TiO_2$, and mixtures thereof; the one or more proton pumping photoactive biological layers being deposited on the second conductive metallic material;
and
   vii) the layer of a visible or UV and visible radiation transparent conductor material (7) selected from graphene; carbon nanotubes (CNT); ultra thin metal films; Fluorine doped Tin Oxide (FTO) coated glass; Transparent Conductive Oxides (TCO); transparent conducting polymers; Poly(3,4-ethylenedioxythiophene) (PEDOT); Poly(3,4-ethylenedioxythiophene) PEDOT: poly(styrene sulfonate) PSS; and Poly(4,4-dioctyl cyclopentadithiophene).

5. The device according to claim 1, wherein the second compartment (B) comprise the following elements extending from its front end surface which it is in contact with the polymeric membrane to its opposing back end surface:
   i) optionally, a layer of a visible or UV and visible radiation transparent conductor material (8) selected from graphene; carbon nanotubes (CNT); ultra thin metal films; Fluorine doped Tin Oxide (FTO) coated glass; Transparent Conductive Oxides (TCO); transparent conducting polymers; Poly(3,4-ethylenedioxythiophene) (PEDOT); Poly(3,4-ethylenedioxythiophene) PEDOT: poly(styrene sulfonate) PSS; and Poly(4,4-dioctyl cyclopentadithiophene);
   ii) a third conductive metallic material (9) selected from platinum, gold, silver, graphite, aluminum, $TiO_2$, carbon nanotubes, graphene, reduced graphene oxide (rGO), $TiO_2$ doped by Au nanoparticles, Au nanoparticles doped by palladium nanoparticles, $TiO_2$ doped by Pt nanoparticles, $TiO_2$/rGO, Pt/Co/$TiO_2$, and $TiO_2$ doped by Ag nanoparticles and mixtures thereof; the third conductive metallic material working as a cathodic electrode;
   and
   iii) the hydrogen collecting deposit (B2).

6. The device according to claim 1, wherein the first photoanode electrode (A1) comprises a first conductive metallic material (2) content from 0.02 $mg/cm^2$ to 5 $mg/cm^2$.

7. The device according to claim 1, wherein the second electrode (A2) comprises a second conductive metallic material (6) content from 0.01 $mg/cm^2$ to 5 $mg/cm^2$.

8. The device according to claim 1, wherein the third electrode (B1) comprises a third conductive metallic material (9) content from 0.02 $mg/cm^2$ to 5 $mg/cm^2$.

9. The device according to claim 1, comprising between 100-400 layers of the proton pumping photoactive biological layer (3) on the first conductive metallic material (2) of the first photoanode electrode.

10. The device according to claim 1, comprising between 100-400 layers of the proton pumping photoactive biological layer (5) on the second conductive metallic material (6) of the second electrode.

11. The device according to claim 1, wherein the one or more proton pumping photoactive biological layers (3) and (5) comprise oriented purple membrane containing bacteriorhodopsin protein or any of its genetic variants.

12. The device according to claim 1, wherein the one or more proton pumping photoactive biological layers (3) and (5) comprise oriented purple membrane containing a bacteriorhodopsin genetic variant wherein one or more aminoacids of the amino acid sequence in the bacteriorhodopsin protein are replaced with one or more aminoacids that are different from that of the wild type *H. salinarum* bacteriorhodopsin protein.

13. The device according to claim 1, wherein the one or more proton pumping photoactive biological layers (3) and (5) comprise oriented purple membrane containing a bacteriorhodopsin genetic variant which is selected from those wherein one or more aminoacids of the amino acid sequence in the bacteriorhodopsin protein to the loops that are in the intracellular part are replaced with one or more cysteine aminoacids; or alternatively from those wherein one or more glutamic acid of the amino acid sequence in the bacteriorhodopsin protein to the loops that are in the extracellular part are replaced with one or more glutamine aminoacid.

14. The device according to claim 1, wherein the bacteriorhodopsin genetic variant is selected from V101C, M163C, A160C, T247C, E166C, E74Q, E194Q and E194Q/E204Q.

15. A photoelectric conversion element comprising: the bio sensitized photoelectric conversion device as defined in claim 1.

* * * * *